US010214450B2

(12) United States Patent
Grün et al.

(10) Patent No.: US 10,214,450 B2
(45) Date of Patent: Feb. 26, 2019

(54) HARDENER COMPOSITION FOR ADDITION-POLYMERISATION-BASED SYNTHETIC FIXING MORTAR SYSTEMS, AND THE USE AND PRODUCTION THEREOF

(71) Applicant: fischerwerke GmbH & Co. KG, Waldachtal (DE)

(72) Inventors: Jürgen Grün, Bötzingen (DE); Martin Vogel, Glottertal (DE); Christian Schlenk, Denzlingen (DE); Christian Weinelt, Teningen (DE)

(73) Assignee: FISCHERWERKE GMBH & CO. KG, Waldachtal (DE)

( * ) Notice: Subject to any disclaimer, the term of this patent is extended or adjusted under 35 U.S.C. 154(b) by 29 days.

(21) Appl. No.: 15/508,568

(22) PCT Filed: Sep. 9, 2015

(86) PCT No.: PCT/EP2015/001813
§ 371 (c)(1),
(2) Date: Mar. 3, 2017

(87) PCT Pub. No.: WO2016/041625
PCT Pub. Date: Mar. 24, 2016

(65) Prior Publication Data
US 2017/0253529 A1    Sep. 7, 2017

(30) Foreign Application Priority Data

Sep. 17, 2014  (DE) .......................... 10 2014 013 695
Jul. 15, 2015   (DE) .......................... 10 2015 111 484

(51) Int. Cl.
| | |
|---|---|
| *C08G 18/10* | (2006.01) |
| *C04B 24/42* | (2006.01) |
| *C08G 77/04* | (2006.01) |
| *C08K 5/544* | (2006.01) |
| *C08K 5/548* | (2006.01) |
| *C08L 63/00* | (2006.01) |
| *C08L 75/00* | (2006.01) |
| *C08L 83/08* | (2006.01) |
| *C08G 59/40* | (2006.01) |
| *C04B 28/04* | (2006.01) |
| *C07F 7/18* | (2006.01) |
| *C04B 40/06* | (2006.01) |
| *C04B 26/14* | (2006.01) |
| *C04B 26/16* | (2006.01) |
| *C04B 111/00* | (2006.01) |
| *C04B 103/14* | (2006.01) |

(52) U.S. Cl.
CPC .............. *C04B 24/42* (2013.01); *C04B 26/14* (2013.01); *C04B 26/16* (2013.01); *C04B 28/04* (2013.01); *C04B 40/065* (2013.01); *C07F 7/18* (2013.01); *C08G 18/10* (2013.01); *C08G 59/4085* (2013.01); *C08G 77/045* (2013.01); *C08K 5/544* (2013.01); *C08K 5/548* (2013.01); *C08L 63/00* (2013.01); *C08L 75/00* (2013.01); *C08L 83/08* (2013.01); *C04B 2103/14* (2013.01); *C04B 2111/00715* (2013.01)

(58) Field of Classification Search
None
See application file for complete search history.

(56) References Cited

U.S. PATENT DOCUMENTS

| | | | | |
|---|---|---|---|---|
| 3,532,653 A | * | 10/1970 | Smeal ..................... | C08G 59/50 523/450 |
| 4,652,662 A | * | 3/1987 | von Au ................... | C08G 77/08 549/215 |
| 4,673,750 A | * | 6/1987 | Beers ...................... | C07F 7/1868 524/267 |

(Continued)

FOREIGN PATENT DOCUMENTS

| | | |
|---|---|---|
| DE | 101 32 941 A1 | 1/2003 |
| DE | 101 32 942 A1 | 1/2003 |

(Continued)

OTHER PUBLICATIONS

International Search Report and Written Opinion for corresponding International Application No. PCT/EP2015/001813 dated Nov. 9, 2015.

(Continued)

*Primary Examiner* — Robert S Loewe
(74) *Attorney, Agent, or Firm* — Renner, Otto, Boisselle & Sklar, LLP

(57) ABSTRACT

Hardener composition for an addition-polymerization-curable synthetic fixing mortar system for embedding anchoring means in mortar in holes or crevices, wherein the hardener composition includes oligomeric siloxanes having on average per molecule at least one or preferably two or more organic radicals that carry one or more (secondary or primary) amino and/or thiol groups that react with isocyanate or epoxy groups in the addition reaction and having on average per molecule at least one or more hydrolysable groups, and, in addition, can include one or more further customary additives, to synthetic fixing mortar systems including such a hardener composition, to the use of such synthetic fixing mortar systems for embedding anchoring means in mortar in holes or crevices and to methods of producing and using the synthetic fixing mortar systems and the hardener composition.

16 Claims, No Drawings

(56) References Cited

U.S. PATENT DOCUMENTS

| | | | | |
|---|---|---|---|---|
| 4,689,390 A * | 8/1987 | Suzuki | ............... | C08G 59/10 528/104 |
| 5,051,129 A * | 9/1991 | Cuthbert | ............... | C04B 41/009 106/2 |
| 5,229,438 A * | 7/1993 | Ishida | ............... | C04B 26/14 523/428 |
| 5,889,125 A | 3/1999 | Neumann et al. | | |
| 5,942,073 A * | 8/1999 | Mowrer | ............... | B32B 27/08 156/329 |
| 6,663,705 B2 * | 12/2003 | Fukasawa | ............... | C09J 183/08 106/287.11 |
| 6,727,339 B2 | 4/2004 | Luginsland et al. | | |
| 6,903,177 B2 * | 6/2005 | Seo | ............... | C07F 7/21 106/11 |
| 6,946,537 B2 | 9/2005 | Krafczyk et al. | | |
| 7,223,821 B2 * | 5/2007 | Okuhira | ............... | C08G 18/10 525/476 |
| 7,264,669 B1 * | 9/2007 | Tomasino | ............... | C08G 77/54 106/287.11 |
| 7,605,220 B2 * | 10/2009 | Wakabayashi | ............... | C08K 5/09 528/14 |
| 7,931,773 B2 * | 4/2011 | Mahdi | ............... | C03C 25/26 156/108 |
| 2006/0135656 A1 | 6/2006 | Briand et al. | | |
| 2009/0305051 A1 * | 12/2009 | Corsaro | ............... | C09J 5/02 428/423.1 |
| 2009/0318614 A1 * | 12/2009 | Chevalier | ............... | C09C 1/0093 524/588 |
| 2011/0190420 A1 | 8/2011 | Nagelsdiek et al. | | |
| 2016/0355437 A1 | 12/2016 | Grun et al. | | |

FOREIGN PATENT DOCUMENTS

| | | |
|---|---|---|
| DE | 10 2013 113 465 A1 | 6/2014 |
| EP | 0 824 124 A1 | 2/1998 |
| WO | WO 02/079293 A1 | 10/2002 |
| WO | WO 02/079341 A1 | 10/2002 |
| WO | WO 2005/090433 A1 | 9/2005 |
| WO | WO 2013/174189 A1 | 11/2013 |

OTHER PUBLICATIONS

English translation of International Preliminary Report on Patentability for corresponding International Application No. PCT/EP2015/001813 dated Mar. 21, 2017.

* cited by examiner

HARDENER COMPOSITION FOR ADDITION-POLYMERISATION-BASED SYNTHETIC FIXING MORTAR SYSTEMS, AND THE USE AND PRODUCTION THEREOF

The invention relates to a hardener composition for synthetic fixing mortar systems which (on use) harden (or, prior to use, are "hardenable") by addition polymerisation for embedding anchoring means in mortar in holes or crevices, especially those based on epoxide and/or on polyurethane, to synthetic fixing mortar systems including such a hardener composition, to the use of such synthetic fixing mortar systems for embedding anchoring means in mortar in holes or crevices and to methods of producing and using the synthetic fixing mortar systems and the hardener composition and to further subject matter of the invention apparent hereinbelow.

Especially suitable synthetic fixing mortar systems are those based on epoxides, such as especially consisting of glycidyl compounds, and suitable hardeners. For example, FIS EM 390 S® (fischerwerke GmbH & Co. KG, Waldachtal, Germany) is a very successful example, well established on the market, of a two-component injectable mortar system for embedding anchoring elements in mortar based on such an epoxy resin in a component A and amines as such a hardener in a further component B, in addition to further constituents in each component.

Other known systems based on addition polymerisation are those based on polyurethanes and/or polyureas.

The use of monomeric silanes (for example of glycidyl silanes and/or aminosilanes) inter alia as adhesion promoter in coating systems or as anti-corrosion agents is known (see, for example, US 2006/0135656 A1).

However, monomeric silanes having hydrolysable (for example silicon-bonded alkoxy) groups have the disadvantage that on hydrolysis during use they release enormous amounts of volatile organic compounds (VOC), for example alcohols.

In addition, in the field of synthetic fixing mortar systems, new restrictions have been placed on manufacturers also in respect of synthetic fixing mortars based on epoxy resins, according to which, in particular, certain low-molecular-weight compounds are to be avoided in order to reduce, for example, health risks and/or ecological risks.

Such statutory regulations or conditions are laid down, for example, by the Chemicals or "REACH" Directive (Directive (EC) No. 1907/2006) in Europe. It can be advantageous, for example, to use those hardener and epoxy components which fulfil the definition of a polymer according to REACH, that is to say that the resins and preferably also the starting materials have a molecular weight distribution such that no single molecule species is present in a proportion of more than 50% by weight and at the same time more than 50% by weight of the chains are composed of at least 3n+1 covalently bonded monomer units.

The afore-mentioned statutory regulations mean that the number of amines that can be used without major restrictions for the formulation of hardener compositions for epoxy resins in the fixings sector is becoming increasingly small. The remaining amines often allow only inadequate scope for establishing desirable properties (high bond stress, high pull-out values, rapid curing, high thermal strength, curing even at low temperature, water-resistance for use in a wet substrate (for example wet concrete), chemical stability and so forth) that are to be achieved in the finished products.

In particular, the achievement of suitable bond stresses, and also the improvement of one or more of the other properties mentioned, by the provision of new components and, in particular, new amine components as hardeners therefore remain objectives to be pursued.

To solve the problems described above, in a general embodiment of the invention there are proposed synthetic fixing mortar systems, for example in the form of 2-component or, furthermore, 3-component fixing kits, with siloxanes which have been oligomerised by means of a hydrolysis and condensation reaction. The oligomerisation and the associated increase in functionality per molecule (for example of amino groups) results not only in increased crosslinkability but also—especially in the case of aminosilanes on account of their basic character (which already have an inherently basically catalysing action)—in the formation of particular, three-dimensionally crosslinked and, especially, close-meshed, hard Si—O structures, with the result that, for example, the crosslinking density and the glass transition temperature of the synthetic fixing mortar systems obtainable after crosslinking can be increased.

Preferably the hardener compositions and/or the oligomerised siloxanes fulfil the above-described definition of a polymer according to "REACH". In certain cases this can result in a reduction in dangerous properties (for example irritant and corrosive action, volatility, skin absorption, danger to the environment) and accordingly in a lower hazard classification. The oligomerisation can take place either before packaging or after packaging (for example in a cartridge), or both. Especially in the former case this results in a reduced VOC content, with the result that the release of outgassing organic compounds can be reduced. A further advantage is that, in comparison with other established amine hardeners that are polymeric in accordance with "REACH" (for example Mannich bases, Bucherer adducts, Michael adducts, addition products and the like), oligomerised siloxanes can have a tendency towards lower viscosities. A particular and further advantage results from the internal acceleration of the reaction with epoxy- and/or isocyanate-based synthetic resins that is possible as a result of the condensation of different silanes (such as, for example, aminosilanes with thiosilanes).

Against this background, the invention relates specifically to the following forms of implementation/embodiments (according to the invention):

A first embodiment of the invention relates to a hardener composition for addition-polymerisation-based synthetic fixing mortar systems for embedding anchoring means in mortar in holes or crevices, especially those based on epoxy- and/or isocyanate-based reactive synthetic resins, wherein the hardener composition includes oligomeric siloxanes having on average per molecule at least one or preferably two or more, organic radicals that carry one or more (secondary or preferably primary) amino and/or thiol groups (—SH) that react with isocyanate or epoxy groups in the addition reaction and having on average per molecule at least one or preferably more hydrolysable groups, and, in addition, can include one or more further customary additives.

A further embodiment of the invention relates to a synthetic fixing mortar system for embedding anchoring means in mortar in holes or crevices, which includes a hardenable epoxy- and/or isocyanate-based reactive synthetic resin and a hardener composition, wherein the hardener composition includes oligomeric siloxanes having on average per molecule more than one, preferably two or more, organic radicals that carry one or more (secondary or preferably primary) amino and/or thiol groups that react with isocyanate or epoxy groups in the addition reaction and having on average per molecule one or preferably more hydrolysable groups, and, in addition, can include one or more further customary additives.

In a further embodiment the invention relates to the use of a synthetic fixing mortar system just described or described hereinbelow for embedding anchoring means in mortar in holes and crevices.

A further embodiment of the invention relates to a process or a method for fixing anchoring elements in holes or crevices, wherein a synthetic fixing mortar system according to the invention described hereinabove and hereinbelow and an anchoring means are introduced successively, especially first the synthetic fixing mortar system and then the anchoring means, and/or (at least substantially) simultaneously into a hole or crevice in a substrate.

Further embodiments of the invention relate to the production of a synthetic fixing mortar system according to the invention, especially (i) with the production of a hardener composition according to the invention described hereinabove or herein-below and especially further (ii) using a hardener composition according to the invention described hereinabove or hereinbelow.

The invention relates further to the use of a hardener composition according to the invention as defined hereinabove and hereinbelow for the production of a synthetic fixing mortar system according to the invention defined hereinabove and hereinbelow, especially characterised in that the hardener composition and a reactive synthetic resin, especially an epoxy- and/or isocyanate-based reactive synthetic resin, hardenable by addition hardening are provided as constituent of components of a multi-component system, especially a two-component system. The invention relates also to the use of a hardener composition according to the invention as hardener in a synthetic fixing mortar system defined hereinabove and hereinbelow.

It has been found, surprisingly, that it is possible not only for there to be relatively high proportions of the siloxane additives in the hardener compositions, but also—in respect of the use as hardener—for the oligomeric siloxanes to be used alone as hardener in the synthetic fixing mortar systems according to the invention. It is also possible, without wishing to be conclusively bound by this attempt at explanation, that the oligomeric siloxanes facilitate improved contact with the wetted substrate surface in the hole or crevice, whether in interlocking engagement and/or in material-bonded engagement.

Surprisingly it has been found that the synthetic fixing mortar systems according to the invention also exhibit especially good properties in respect of their performance in the tension zone, that is to say in cracked concrete, using normal threaded rods. Other mechanical properties can also be positively affected, such as, for example, the maximum elongation at break and the tensile modulus.

The cured compositions are thus preferably high-strength solids having little flexibility and having a tensile modulus >0.5 GPa, preferably >1 GPa, a tensile strength of >1 MPa, preferably >5 MPa, and an elongation at break of <10%, preferably <5%, especially <2% (all three variables measured in accordance with DIN EN ISO 527) and a compressive strength of >5 MPa, preferably >10 MPa, especially >50 MPa or >80 MPa (measured in accordance with DIN EN ISO 604).

The elongation at break is determined more precisely in accordance with DIN EN ISO 527-1 using dumbbell test specimens of type 1 BA (in accordance with DIN EN ISO 527-2) after 7 days storage at room temperature.

Finally, also using methods in accordance with the guidelines of the European Organisation for Technical Approvals (EOTA) (2001): ETAG No. 001, November 2006 edition, Guideline for European Technical Approval of Metal Anchors for Use in Concrete, Part 5: Bonded Anchors, February 2008, the performance in cracked concrete is found to be increased in comparison with corresponding synthetic fixing mortar systems without addition of siloxane.

Further measurement methods that are generally applicable (also applicable generally for synthetic fixing mortar systems other than the exemplified systems disclosed herein) can be found in the Examples.

By means of the definitions given above and below it is possible hereinabove and hereinbelow for one, some or all of the broader features, terms or symbols used to be replaced by the respective more specific said features, terms or symbols, resulting in preferred forms of implementation of the invention.

Where weights are given in percent (% by weight), unless otherwise specified they relate to the total mass of the reactants and additives of the synthetic fixing mortar system (that is to say the constituents present in the composition to be cured after mixing, without packaging and other possible parts, such as static mixers or the like).

The oligomeric siloxanes having on average per molecule (based only on the siloxane oligomers) more than one, for example two or more, organic radicals that carry one or more (secondary or preferably primary) amino and/or thiol groups that react with isocyanate or epoxy groups in the addition reaction and having on average per molecule of oligomer one or preferably more hydrolysable groups, are siloxane oligomers which are functionalised with amino and/or thiol groups and which have per molecule of oligomer at least one (preferably two or more) amino and/or thiol groups and at least one, preferably at least two, hydrolysable groups bonded to silicon. They have Si—O-crosslinked structural elements which form at least one structure selected from chain-like, cyclic, crosslinked and optionally three-dimensionally crosslinked structures, and they include preferably at least one structure in idealised form of the general formula (I),

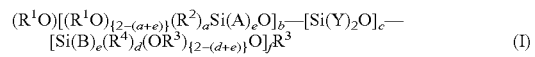

$$(R^1O)[(R^1O)_{\{2-(a+e)\}}(R^2)_aSi(A)_eO]_b-[Si(Y)_2O]_c-[Si(B)_e(R^4)_d(OR^3)_{\{2-(d+e)\}}O]_fR^3 \quad (I)$$

wherein the structural elements are derived from alkoxysilanes and

A and B each independently of the other are (preferably $C_1$-$C_7$)alkyl that includes at least one (primary or secondary) amino and/or thiol group;

Y denotes $OR^5$ and/or $R^5$ or, in crosslinked and optionally three-dimensionally crosslinked structures, independently of any other denotes $OR^5$, $R^5$ or $O_{0.5}$; preferably Y is $OR^5$;

the radicals $R^1$, $R^2$, $R^3$, $R^4$ and $R^5$, each on its own and independently of one another, denote an unsubstituted or, furthermore, substituted—optionally, furthermore, heteroatom-containing—linear, branched or cyclic alkyl radical having from 1 to 20 carbon atoms;

and a, b, c, d, e and f, based on a structural unit, independently of one another denote whole numbers, wherein a independently of any other is 0 or 1 or 2;

b is 1 or more;

c is 0 or more;

d independently of any other is 0 or 1 or 2;

e independently of any other is 1 or 2; and f is 0 or more, for example (based only on the oligomer molecules) is 1 or more;

with the proviso that b+c+f is 2 or more, for example 2.001 or more.

The limits are given by the tetravalency of silicon.

Where more than one structural element (A1) equal to —[(R$^1$O)$_{\{2-(a+e)\}}$(R$^2$)$_a$Si(A)$_e$O]$_b$—(b>1) and/or (A2) equal to [Si(B)$_e$(R$^4$)$_d$(OR$^3$)$_{\{2-(d+e)\}}$O]$_f$— (f>1) and/or (A3) equal to —[Si(Y)$_2$O]$_c$—(c>1) is present, the mentioned structural elements do not have to be arranged in succession—as shown in formula (I)—but can also be distributed randomly (for example, purely by way of illustration and without implying any limitation: A1-A1-A3-A1 A2-A1-A3).

The oligomeric siloxanes used according to the invention especially preferably include one or more compounds having at least one structure in idealised (statistically averaged) form of the general formula (IA),

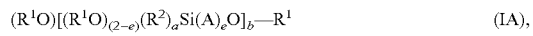

$$(R^1O)[(R^1O)_{(2-e)}(R^2)_aSi(A)_eO]_b—R^1 \quad (IA),$$

wherein in a further preferred form of implementation all radicals R$^1$ for each molecule can be identical;

wherein mixtures of two or more compounds of the formula (IA) having different radicals R$^1$ are also possible;

and the A groups independently of other A groups in the same or other molecules can have the different functional groups defined above (amino or thio or both) and different functionalities, wherein, in the compounds of the formula (IA), R$^1$, R$^2$, a and e are as defined above for structures of the formula I and on average b is equal to or greater than 2.000.

Furthermore, the oligomeric siloxanes used according to the invention can also additionally have trialkylsilane groups such as trimethylsilane or triethylsilane groups, for example as a result of preparation using alkoxytrialkylsilane, which allows the degree of oligomerisation to be adjusted: the alkoxytrialkylsilanes can, for example when added at a specific point in time, bring about a chain termination.

"Include" or "comprise" means that other components or features may be present in addition to the components or features mentioned and therefore does not refer to an exhaustive list, unlike "contain", the use of which does signify an exhaustive list of components or features.

Where the attribute "furthermore" is mentioned, this means that features without this attribute can be more preferred.

Si-bonded hydrolysable groups are to be understood as being especially such groups selected from the group consisting of halogen, such as chloro, acyloxy, aryloxy, aralkyloxy (=arylalkyloxy) and especially alkoxy. Methoxy or ethoxy are especially preferred.

(M)ethoxy denotes methoxy, ethoxy or methoxy and ethoxy (as a mixture).

The organic radicals carrying (secondary or preferably primary) amino and/or thiol groups that react with isocyanate or epoxy groups in the addition reaction are preferably organic radicals having from 1 to 20 carbon atoms in the basic structure, preferably having from 2 to 10 and especially from 1 to 7 carbon atoms, which can be aromatic, alicyclic or aliphatic (then alkyl) and which carry one or more (for example from 1 to 3) thiol, primary amino and/or secondary amino groups (for example R—NH—, wherein R is (especially C$_1$-C$_7$)alkyl, phenyl-C$_1$-C$_7$alkyl, cycloalkyl or cycloalkyl-C$_1$-C$_7$alkyl) as functional groups. Special preference is given to amino(especially C$_1$-C$_7$)alkyl or mercapto (especially C$_1$-C$_7$)alkyl carrying a plurality of or especially one such thiol, primary amino and/or secondary amino groups. Examples of preferred such radicals are 3-aminopropyl, N-(2-aminoethyl)-3-aminopropyl, N-cyclohexyl-3-amino-propyl, N-cyclohexylaminomethyl, N-phenylaminomethyl, N-cyclohexylaminomethyl, 3-[2-(2-aminoethylamino)ethylamino]propyl and 3-mercaptopropyl.

Preferred starting materials for the production of such oligomeric siloxanes comprise N-(2-aminoethyl)-3-aminopropyltri(m)ethoxysilane, N-(2-aminoethyl)-3-aminopropyl-methyldi(m)ethoxysilane, 3-aminopropyltri(m)ethoxysilane, N-cyclohexyl-3-amino-propyltri(m)ethoxysilane, 3-mercaptopropyltri(m)ethoxysilane, phenylaminomethyltri(m)ethoxysilane, phenylaminopropyltri(m)ethoxysilane, or 3-[2-(2-aminoethylamino)-ethylamino]propyltri(m) ethoxysilane, or combinations of two or more thereof.

The following may be mentioned as preferred starting materials of the formula IV: all silanes which lead in the siloxane oligomer to the formation of D, T and Q structural units. For the more precise nomenclature of the naming of such siloxane structures, reference may be made to "Römpp Chemielexikon" headword: Silicones.

In addition to the oligomeric siloxanes, the synthetic fixing mortar systems according to the invention can also include (for example for establishing a suitable viscosity) monomeric silane additives as (at least partially) reactive diluents. The monomeric silanes can be selected, for example, from the group which consists especially of N-(2-aminoethyl)-3-aminopropyltri(m)ethoxysilane, N-(2-aminoethyl)-3-aminopropylmethyl-di(m)ethoxysilane, 3-aminopropyltri(m)ethoxysilane, N-cyclohexyl-3-aminopropyl-tri(m)ethoxysilane, 3-mercaptopropyltri(m)ethoxysilane, phenylaminomethyl-tri(m)ethoxysilane, phenylaminopropyltri(m)ethoxysilane, or 3-[2-(2-aminoethylamino)-ethylamino]propyltri(m)ethoxysilane, and/or tetraalkoxysilane, such as tetraethoxy-silane, tetramethoxysilane or tetrapropoxysilane or alkoxypolysilicate, such as ethyl or propyl polysilicate; or mixtures of two or more thereof, and can also be unreacted starting materials.

The siloxanes (especially the oligomeric siloxanes according to the invention) can be provided, for example, based on the total synthetic fixing mortar system, in a proportion by weight of up to (a maximum of) 50% by weight, especially from 0.001 to 50% by weight, such as from 0.01 to 30% by weight, for example from 0.1% by weight or more, such as from 0.5 to 20 or to 15% by weight, from 1% by weight or more, such as from 2 to 20 or to 10% by weight, or from 3% by weight or more, for example from 3 to 20 or to 6% by weight.

Secondary amino is, for example, a radical of the formula Q-NH—, in which Q is an unsubstituted or substituted radical selected from C$_1$-C$_7$alkyl (especially methyl, ethyl or propyl), C$_3$-C$_7$cycloalkyl (especially cyclohexyl) or C$_6$-C$_{12}$ aryl (especially phenyl). Amino, thio or hydroxy may occur as substituents.

Where hetero atoms are mentioned (also in the case of heteroaliphatic or heterocyclo-aliphatic compounds which may have, for example, from 1 to 20 chain atoms or 3 to 20 ring atoms, respectively), they are preferably from 1 to 3 hetero atoms which are selected independently of one another from O, S and N.

The addition-polymerisation-based synthetic fixing mortar systems are especially reactive synthetic resins based on epoxides and/or on isocyanates.

The epoxy-based reactive synthetic resins that can be used during the use of or in synthetic fixing mortar systems according to the invention include an epoxy component, preferably based on glycidyl compounds, for example those having an average glycidyl group functionality of 1.5 or greater, especially of 2 or greater, for example from 2 to 10, which can optionally include further glycidyl ether(s) as reactive diluent. The epoxides of the epoxy component are preferably poly(including di)-glycidyl ethers of at least one polyvalent alcohol or phenol, such as novolak, bisphenol F or bisphenol A, or mixtures of such epoxies, for example obtainable by reaction of the corresponding polyvalent alcohols with epichlorohydrin. Examples are hexanediol diglycidyl ether, trimethylolpropane triglycidyl ether, novolak epoxy resins, bisphenol A epichorohydrin resins and/or bisphenol F epichorohydrin resins, for example having an average molecular weight of 2000. The epoxy resins can have, for example, an epoxy equivalent of from 120 to 2000, preferably from 150 to 400, such as especially from 155 to 195, for example from 165 to 185. The proportion of epoxy component in the total mass of the reactants and additives of the injectable synthetic mortar system is preferably from 5 to less than 100% by weight, especially from 10 to 80% by weight, from 10 to 70% by weight or from 10 to 60% by weight. Also possible are mixtures of two or more such epoxy components. Suitable epoxy resins, reactive diluents and hardeners are also to be found in the standard work by Lee H. and Neville K., "Handbook of Epoxy Resins" (New York: McGraw-Hill), 1982 (those compounds are incorporated herein by reference).

Important examples of further ingredients are one or more selected from accelerators, reactive diluents, thixotropic agents, fillers and further additives.

As accelerators there may be included, for example, tert-amines, such as imidazoles or tert-aminophenols, such as tris-2,4,6-dimethylaminomethylphenol, organo-phosphines or Lewis bases or Lewis acids, such as phosphoric acid esters, or mixtures of two or more thereof, in one or (especially in the case of multi-component systems) in several of the components, preferably in each case in a hardener component, for example in a proportion by weight of from 0.001 to 15% by weight.

As thixotropic agents there can be used customary rheology aids, such as pyrogenic silicic acid. They can be added, for example, in a proportion by weight of from 0.001 to 50% by weight, for example from 1 to 20% by weight.

As fillers there are used customary fillers, especially cements (for example Portland cements or high-alumina cements), chalks, sand, quartz sand, quartz powder or the like, which can be added in the form of powder, in granular form or in the form of shaped bodies, or other fillers, such as, for example, those mentioned in WO 02/079341 and WO 02/079293 (which in this regard are incorporated herein by reference), or mixtures thereof, it being furthermore or especially possible for the fillers also to be silanised, for example in the form of amino- or epoxy-silane-treated quartz powder, such as Silbond AST or EST® from Quarzwerke GmbH, in the form of amino- or glycidyl-silane-treated silica, such as Aktisil AM or EM® from Hoffmann Mineral, or amino- or glycidyl-silane-treated pyrogenic silicic acids. The fillers can be present in one or more components, for example, of a multi-component kit according to the invention, for example one or both components of a corresponding two-component kit; the proportion of fillers is preferably from 0 to 90% by weight, for example from 10 to 90% by weight. In addition or alternatively, hydraulically hardenable fillers, such as gypsum, calcined chalk or cement (for example alumina cement or Portland cement), water glass or active aluminium hydroxides, or two or more thereof, can be added.

Further additives may also be added, such as plasticisers, non-reactive diluents, flexibilisers, stabilisers, rheology aids, such as thixotropic agents, for example pyrogenic silicic acid, anti-static agents, thickeners, wetting agents, plasticisers such as phthalic acid esters or sebacic acid esters, colouring additives, such as dyes or especially pigments, for example for staining the components different colours for better monitoring of their intermixing, or the like, or mixtures of two or more thereof.

Such further additives can preferably be added or be present in total in proportions by weight of in total from 0 to 90%, for example from 0 to 40% by weight.

Certain of the compounds mentioned in the definition of the epoxides, such as trimethylolpropane triglycidyl ether or hexanediol diglycidyl ether, which have a lower viscosity than epoxides containing aromatic groups, can also be used as reactive diluents, for example in a proportion by weight of from 0.1 to 90% by weight, for example between 0.5 and 75% by weight or between 1 and 40% by weight. Also possible are mixtures of two or more such reactive diluents of different molecular structure and especially of different functionality.

The hardener includes either only the oligomeric siloxanes according to the invention or additionally at least one further compound customarily used for epoxy hardening (reaction partner in the polyaddition), the term "hardener" meaning preferably at least one compound which is customarily used for epoxy hardening, with or without addition of filler, and/or further additives, thickeners and/or further additional ingredients, such as dyes and the like, in other words the complete hardener component. The hardener can be in the form of a separate component and/or can also be incorporated (especially in protected form, that is to say, for example, in micro-encapsulated form) in the reactive resin formulation (in the form of a hardenable component, that is to say one which, after mixing with the epoxy-based reactive synthetic resin after breaking-open of the casing of the microcapsule, cures by means of polymerisation). Customary additives can be added, such as, for example, fillers (especially as defined above) and/or (especially for producing a paste or emulsion) solvents, such as benzyl alcohol. (For example residual) water contents are here likewise not absolutely excluded. Here too, further additional ingredients/additives can arise during storage, such as gases, or especially substances and/or substance mixtures in the gaseous state. The further additives or additional ingredients of the hardener component of a multi-component system according to the invention can be added, for example, in a proportion by weight of in total from 0.001, or 0.01, to 70% by weight, for example from 1 to 40% by weight, based on the hardener component.

The compounds customarily used for epoxy hardening, if desired, in addition to the oligomeric siloxanes used according to the invention (which compounds function as reaction partners in the polyaddition) are especially those having two or more groups selected from amino, imino and mercapto, for example corresponding amines (preferred), thiols or aminothiols, or mixtures thereof, for example as mentioned in Lee H. and Neville K., "Handbook of Epoxy Resins" (New York: McGraw-Hill), 1982, which is incorporated herein by reference in this regard, for example di- or poly-amines mentioned therein, and/or di- or poly-thiols. Preferably the compounds customarily used for epoxy hardening have no rubber modification (for example amino-functionalised butadiene or butadiene/acrylonitrile polymers).

The (additional) compounds (generally) customarily used for epoxy hardening comprise, for example, in a form of implementation of the invention:

di- or poly-amines, such as especially aliphatic (such ethylenediamine), hetero-aliphatic (such as 4,9-dioxadodecane-1,12-diamine), cycloaliphatic (such as 1,3-bis(aminomethyl)cyclohexane), cycloheteroaliphatic (such as aminoethylpiperazine), araliphatic (such as meta-xylylenediamine) and aromatic di- or poly-amines, amidoamines, amine adducts, polyether diamines or polyphenyl/polymethylene-polyamines, Mannich bases (especially as disclosed in the publication EP 0 645 408 B1 and WO 2005/090433, especially on page 3, last paragraph, to page 6, second paragraph, such as in Example 1 or especially Example 2 thereof, which in this regard is incorporated herein by reference, alone or in admixture with one or more further di- or poly-amines), amines in accordance with the as yet unpublished German patent application DE 10 2013 113 465.3 and EP 0 824 124 A1, polyamides and the like; —di- or poly-thiols, for example: ethoxylated and/or propoxylated alcohols of mono-, di-, tri-, tetra-, penta-ols and/or other polyols with thiol end groups (for example Capcure 3-800 from Cognis) and/or thiols that include ester groups. These may be, for example, esters of α-mercaptoacetate or β-mercaptopropionate with diols, triols, tetraols, pentaols or other polyols.

It is also possible for mixtures of two or more of the mentioned compounds customarily used for epoxy hardening to be used or included.

The additional or supplementary compounds customarily used for epoxy hardening, if present, are preferably provided in amounts of up to 95% by weight, preferably from 2 to 70% by weight, based on the total mass of the reactants and additives of the composition of the synthetic fixing mortar system to be cured.

Based on the hardener component, the proportion of such compounds in a possible preferred form of implementation of the invention is from 1 to 95% by weight, for example from 3 to 90% by weight, for example from 4 to 95% by weight, from 5 to 90% by weight or from 10 to 80% by weight, or they are absent (0% by weight).

The isocyanate-based reactive synthetic resins that can be used, furthermore, during the use of or in synthetic fixing mortar systems according to the invention are selected from (monomeric and/or oligomeric and/or polymeric (for example polynuclear)) mono-, di- or poly-isocyanates and isocyanate prepolymers customary in polyurethane and/or polyurea chemistry.

Suitable isocyanates include especially aryl-di- or aryl-poly-isocyanates, for example TDI (toluenediisocyanate, such as toluene-2,4- or -2,6-diisocyanate), diisocyanato-diphenylmethane, preferably MDI or especially PMDI (product of (especially technical) MDI in which further phenylene and/or phenylene isocyanate radicals are present in addition to the two biphenylene units in MDI, which allows an increased molecular weight, higher viscosity and advantageously a low vapour pressure and accordingly low health hazard), 4,4'-isopropylidene-diphenylisocyanate, 2,4,4'-triisocyanato-diphenylmethane and xylene-1,3- or 1,4-diisocyanate.

Di- or poly-isocyanates are furthermore aliphatic, cycloaliphatic or the mentioned aromatic di- or poly-isocyanates, or aromatic di- or poly-isocyanates other than those already mentioned, especially di-, tri- or tetra-isocyanates, especially hexane-diisocyanate, 4,4'-diisocyanatodicyclohexyl-methane, isophorone diisocyanate, 1-methylcyclohexane-2,4- or -2,6-diisocyanate, 3-isocyanatomethyl-3,5,5-trimethylcyclo-hexylisocyanate; or crude polyisocyanates; or prepolymers having two or more isocyanato groups; or mixtures of two or more of the mentioned di- or poly-isocyanates. Special preference is given to isocyanates having an average NCO functionality of 2-5.

The last-mentioned prepolymers having two or more isocyanato groups are especially those formed by reaction starting from di- or poly-isocyanates, especially those mentioned in the last paragraph except for the prepolymers themselves, with as appropriate difunctional or higher functional alcohols (diols or polyols), amines, amino alcohols, thiols, aminothioalcohols, aminothiols or amino-, thio- and hydroxy-carrying alkanes, or mixtures of two or more thereof. Examples of polyisocyanate prepolymers can be found in WO 02/079341 A.

The isocyanates can also be present partly or entirely in the form of resins carrying isocyanate radicals at least some of which are in the form of biuret, allophanate, uretdione, isocyanurate, iminooxadiazinedione and/or uretonimine groups as a result of reaction with one another.

The proportion of the monomeric and/or oligomeric and/or polymeric (for example polynuclear) di- or poly-isocyanates is, for example in a possible preferred form of implementation of the invention, up to 90% by weight, for example from 10 to 90% by weight, for example between 30 and 70% by weight.

The hardeners required for, for example, polyurethanes, polyureas and polyurethane/polyurea mixed polymers, namely polyols, polyamines, polymercaptans and polyamino alcohols or further compounds mentioned above as hardeners in the case of the prepolymers, or isocyanates themselves, are known, for example they correspond to the divalent or higher-valent alcohols, mercaptans, amines etc., or di- or poly-isocyanates, mentioned above for forming prepolymers or to those mentioned in WO 02/079341 and WO 02/079293, so that in this regard those applications are incorporated herein by reference.

The components for isocyanate-based synthetic resins can have been pre-accelerated with customary pre-accelerators.

Further additional ingredients such as fillers, additives, accelerators, thixotropic aids etc.—as defined above for epoxy resins—can be present in amounts as defined therefor.

Hardeners (both in the case of the epoxides and in the case of the isocyanates) can be present in a proportion of from 10 to 80% by weight, for example from 25 to 70% by weight.

"Epoxy-based reactive synthetic resin" or "isocyanate-based reactive synthetic resin" means especially that the synthetic fixing mortar systems according to the invention can include, in addition to the constituents mentioned hitherto, also further customary constituents (for example additives or other constituents mentioned above or below). Such further constituents can be present, for example, in an amount of in total up to 80% by weight, preferably between 0.01 and 65% by weight. Even where "based on" is not expressly mentioned, such customary constituents are also included.

A hole or crevice is to be understood as being a hole or crevice that is present in a solid subsurface (substrate) (especially already completed as such), especially masonry or concrete, optionally also in a cracked substrate, such as cracked concrete, and is accessible from at least one side, for example a drilled hole, or furthermore a recessed region made during mortaring with inorganic mortaring or plastering materials (such as cement or gypsum), or the like.

In a special and advantageous form of implementation of the invention, the hardenable components and the associated hardeners (hardener components) are stored separately from one another in a two-component or multi-component system before they are mixed with one another at the desired site (for example close to or in a hole or crevice, such as a drilled hole).

The synthetic fixing mortar systems according to the invention are then provided in the form of multi-component systems (for example a multi-component kit) and are also used as such.

A multi-component kit is understood to be especially a two-component or (furthermore) multi-component kit (preferably a two-component kit) having a component (A), which comprises either one or more reactive synthetic resins that are hardenable by polyaddition (=hardening after addition of at least one (in each case suitable) hardener)), especially reactive synthetic resins based on epoxides and/or on isocyanates, and having a component B, which comprises the respectively associated hardener as defined hereinabove and hereinbelow, it being possible for further additives to be provided in one or both of the components, preferably a two-chamber or furthermore multi-chamber apparatus, wherein the components (A) and (B) that are able to react with one another and optionally further separate components are present in such a way that their constituents cannot react with one another (especially not with curing) during storage, preferably in such a way that their constituents do not come into contact with one another prior to use, but that enables components (A) and (B) and optionally further components to be mixed together for fixing at the desired location, for example directly in front of or in a hole, and, if necessary, introduced in such a way that the hardening reaction can take place therein. Also suitable are capsules, for example made of plastics, ceramics or especially glass, in which the components are arranged separated from one another by means of rupturable boundary walls (which can be ruptured, for example, when an anchoring element is driven into a hole or crevice, such as a drilled hole) or integrated separate rupturable containers, for example in the form of capsules, such as ampoules, arranged one inside the other; and also especially multi-component or preferably two-component cartridges (which are likewise especially preferred), the chambers of which contain the plurality of components or preferably the two components (especially (A) and (B)) of the synthetic fixing mortar composition according to the invention having the compositions mentioned hereinabove and hereinbelow for storage prior to use, the kit in question preferably also including a static mixer.

The systems are especially two-component systems in which the ratio by weight of component A to component B is from 99:1 to 1:99, from 99:1 to 50:50, from 99:1 to 60:40 or from 99:1 to 70:30.

The synthetic fixing mortar systems according to the invention (preferably synthetic fixing mortar kits) can consequently preferably be provided and also used in the form of two-component or multi-component systems (multi-component kit). Two-component systems can also be those which include one component, for example in encapsulated form, in the other component.

The use of a synthetic fixing mortar system according to the invention at the desired site of use is effected by mixing the associated components (which are separate prior to mixing to inhibit reaction), especially close to and/or directly in front of a hole or (for example especially when cartridges having static mixers are used) directly in front of and/or (especially when suitable capsules or ampoules are ruptured) inside a hole or crevice, for example a drilled hole.

"Embedding in mortar" is especially to be understood as meaning (material-bonded and/or interlocking) fixing of anchoring means made of metal (for example undercut anchors, threaded rods, screws, drill anchors, bolts) or, furthermore, made of some other material, such as plastics or wood, in solid substrates (preferably already completed as such), such as concrete or masonry, especially insofar as they are components of artificially erected structures, more especially masonry, ceilings, walls, floors, panels, pillars or the like (for example made of concrete, natural stone, masonry made of solid blocks or perforated blocks, furthermore plastics or wood), especially in holes, such as drilled holes. Such anchoring means can then be used to secure, for example, railings, covering elements, such as panels, façade elements or other structural elements.

Where "mixtures of two or more thereof" are mentioned, this includes especially mixtures of at least one of the mentioned constituents that are highlighted as being preferred with one or more other constituents, especially one or more constituents likewise identified as being preferred.

"Completed as such" means especially that the substrates are, except for possible surface modifications (such as coating, for example plastering or painting) or the like, already complete (for example, as building modules or walls) and are not completed only at the same time as the adhesive or are not made from the latter. In other words: the adhesive is then not itself already-completed substrate.

The installation of the anchoring means preferably takes place only a short time, preferably 30 minutes or less, after the components of the fixing mortar according to the invention have been mixed. In explanation: on mixing and introduction of the components onto or into the desired locations at which anchoring means are to be fixed, a plurality of reactions begin, which reactions lead to curing and take place substantially in parallel and/or with only a very small time interval between them.

Specific forms of implementation of the invention relate also to the variants mentioned in the claims and the abstract—the claims and the abstract are therefore incorporated herein by reference.

The oligomeric siloxanes suitable for use according to the invention can be produced in accordance with or analogously to processes known per se.

Alternatively, they can be produced or are formed during storage of the packaged synthetic fixing mortar systems according to the invention and/or during mixing of the constituents for the preparation of a component, for example component B of the synthetic fixing mortar systems according to the invention in situ in the presence of water (for example a predetermined amount in a component including the starting silanes).

The synthesis of the siloxane oligomers is effected, for example, analogously to the procedures in DE 10 2011 086 862 A1, for example by reaction of a compound or a plurality of compounds of the formula II $$(R^1O)(R^1O)_{\{(3-(a+e))\}}(R^2)_a Si(A)_e \qquad (II),$$

wherein $R^1$, $R^2$, a, A and e are as defined above for compounds of the formula I, with compounds of the formula III $$Si(B)_e(R^4)_d(OR^3)_{\{(3-(a+e))\}}OR^3 \qquad (III)$$

wherein $R^3$, $R^4$, d, B and e are as defined above for compounds of the formula I, (wherein the compounds of formulae II and III may be identical or different from one another), and if desired (if c in formula I is to be equal to or greater than 1) with compounds of the formula IV $$Si(Y^*)_4 \qquad (IV),$$

wherein Y* denotes $OR^5$ and/or $R^5$, wherein $R^5$ is as defined above for compounds of the formula I, with water in a defined molar ratio of water to alkoxy groups of the alkoxysilanes such that—as shown in formula I—hydrolysable alkoxy groups (for example $R^1O$ and/or $R^3O$) are left over.

The general amount of water required for establishing a desired saturation of the alkoxy groups can be calculated, for example (in the absence of compounds of the formula (IV)) in accordance with the following formula:

$n$(water)=[$n$(molecules of formula II)×(4−($a$+$e$))+$n$ (molecules of formula III)×(4−($d$+$e$))]×desired saturation in %/100×0.5.

(n corresponds in each case to the molar amount in moles; the 0.5 at the end means that only half as many moles of water must be added as moles of hydrolysable (e.g. alkoxy) groups of the starting materials of formulae II and III since, after the hydrolysis of one hydrolysable or (alkoxy) group of the compound of formula II or of formula III, one mole of water is consumed per one mole thereof and in the condensation of the silanol groups (hydrolysed alkoxy group), one mole of water is then removed again per two moles of silanol groups of formula II and/or III).

In a possible preferred form of implementation of the invention (considered as an average) b+c+f is equal to or greater than 2.000, for example from 2.000 to 70.000, resulting in especially low-viscosity siloxane oligomers.

In a special and greatly preferred form of implementation, the siloxane oligomer is composed of aminopropyltrimethoxysilane and/or aminopropyltriethoxysilane according to formula (IA), wherein 30.000>b is equal to or especially greater than 2.000:

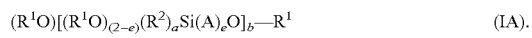
(IA).

In a further possible and especially preferred form of implementation of the invention, in more than 50% (considered as an average) of the siloxane oligomers in formula I b+c+f is equal to or greater than 2, preferably >3 and especially preferably >4, wherein at the same time no single species of the oligomer mixture has a proportion >50%. It is also advantageous if in formula I (again considered as an average) b+c+f<70, especially <50 and very especially preferably <30.

In a further possible special and greatly preferred form of implementation, the siloxane oligomer having structural elements of the formula IA is composed of aminopropyltrimethoxysilane and/or aminopropyltriethoxysilane as starting material(s) so that in more than 50% (considered as an average) of the siloxane oligomers b is equal to or greater than 2.000, preferably >3 and especially preferably >4, wherein at the same time no single species of the oligomer mixture has a proportion >50%. It is also advantageous if (again considered as an average) b<70, especially <50 and more especially <10.

For example, the following procedure may be adopted: the silane or silanes of formulae II, III and optionally IV is/are placed in a reaction flask and then water, which has previously been mixed with a catalyst and a solvent, is slowly metered in at room temperature and normal pressure. When the addition of the solution (water/catalyst/solvent) is complete, the mixture is heated to boiling and maintained under gentle reflux for approximately 4-6 hours. The majority of the solvent and of the catalyst is then distilled off under normal pressure. The residues of solvent and catalyst are then removed with the application of a vacuum at to 100 mbar. The resulting residue is the siloxane oligomer.

The following Examples serve to illustrate the invention but do not limit the scope thereof.

EXAMPLE 1: SYNTHESIS OF A 3-AMINOPROPYLSILOXANE OLIGOMER WITH 45% SATURATION OF THE ALKOXY GROUPS 150 g of 3-aminopropyltrimethoxysilane (Dynasilan® AMMO; Evonik Industries GmbH, Essen, Germany) were placed in a reaction flask. 75 g of methanol (solvent) were mixed with 10.00 g of water and 0.20 g of HCl 37% (catalyst) and transferred to a dropping funnel. At room temperature and normal pressure, slow dropwise addition, with stirring, from the dropping funnel to the 3-aminopropyltrimethoxysilane was carried out. When the addition was complete, the oil bath was heated at 80-100° C. so that the methanol boiled under reflux. After 4-6 hours, the methanol was distilled off as far as possible. The residues of methanol and HCl were then removed with application of a vacuum at a slowly falling pressure to 100 mbar. When 100 mbar was reached, that pressure was maintained for a further 15 minutes. The resulting residue was a 3-aminopropylsiloxane oligomer still having at least 55% hydrolysable residual methoxy groups.

Total formulation:

| Ingredient | Weight introduced [g] |
|---|---|
| AMMO | 150.00 |
| Water | 10.00 |
| HCl 37% | 0.20 |
| Methanol* | 75.00 |

*Water content: 0.05%

The siloxane oligomer prepared according to Example 1 has a mean degree of polymerisation of 3.0 (simplified calculation; for the purposes of illustration only):

$n$(AMMO)/[$n$(AMMO)−$n$(water)]=0.837 mol/[0.837 mol−0.565 mol]=3.07 where $n$(water):$n$ (AMMO)×3×desired saturation in %/100×0.5.

VOC calculation+reduction–with reference to Example 1:
Case a: Use of monomeric AMMO
In Example 1, 150 g of AMMO are used:

| Ingredient | m [g] | M [g/mol] | n [mol] |
|---|---|---|---|
| AMMO | 150.00 | 179.29 | 0.837 |
| Methoxy | | | 2.510 |
| MeOH$_{Ammo}$ | 80.42 | 32.00 | 2.510 |

Accordingly, the VOC content is calculated as follows:

$m$(MeOHAmmo)/$m$(AMMO)×100=% VOC

When monomeric AMMO is used, the VOC content (monomer) is: 53.61%~54% (rounded)
Case b: Use of oligomerised AMMO according to Example 1
In Example 1, 150 g of AMMO are oligomerised with 10.17 g of water:

| Ingredient | m [g] | M [g/mol] | n [mol] |
|---|---|---|---|
| AMMO | 150.00 | 179.29 | 0.837 |
| Water | 10.17 | 18.00 | 0.565 |

-continued

| Ingredient | m [g] | M [g/mol] | n [mol] |
|---|---|---|---|
| Hydrolysed methoxy | | | 1.129 |
| MeOH$_{OUT}$* | 36.19 | 32.00 | 1.129 |

* MeOH$_{OUT}$: methanol removed by hydrolysis

This gives:
Methanol bound in oligomer (m(MeOH$_{oligomer}$)):

$$m(\text{MeOH}_{oligomer}) = m(\text{MeOH}_{AMMO}) - m(\text{MeOH}_{OUT})$$
$$= 44.23 \text{ g Mass } m(\text{oligomer}) = m(\text{AMMO}) - m(\text{MeOH}_{OUT}) + m(\text{water}) = 123.98 \text{ g}$$

Accordingly, the VOC content (oligomer) is calculated as follows:

$$m(\text{MeOH}_{oligomer})/m(\text{oligomer}) \times 100 = 35.68\% \text{ 36\% (rounded)}$$

This corresponds to a VOC reduction of:

$$[\text{VOC content (monomer)} - \text{VOC content (oligomer)}]/\text{VOC content (monomer)} \times 100 = 33.46\%$$

EXAMPLE 2: SYNTHESIS OF A 3-AMINOPROPYL/MERCAPTOPROPYLSILOXANE CO-OLIGOMER WITH 40% SATURATION OF THE ALKOXY GROUPS 60 g of Dynasilan® AMMO and 60 g of 3-mercaptopropyltrimethoxysilane (Dynasilan® MTMO; Evonik Industries GmbH, Essen, Germany) were placed in a reaction flask. 60 g of methanol (solvent) were mixed with 6.79 g of water and 0.16 g of HCl 37% (catalyst) and transferred to a dropping funnel. At room temperature and normal pressure, the resulting mixture was slowly added dropwise from a dropping funnel, with stirring, to the 3-aminopropyltrimethoxysilane/mercaptopropyltrimethoxysilane mixture. When the addition was complete, the oil bath was heated at 80-100° C. so that the methanol boiled under reflux. After 4-6 hours, the methanol was distilled off as far as possible. The residues of methanol and HCl were then removed with application of a vacuum at a slowly falling pressure to 100 mbar. When 100 mbar was reached, that pressure was maintained for a further 15 minutes. The resulting residue was a 3-aminopropyl/mercaptopropylsiloxane co-oligomer still having at least 60% hydrolysable residual methoxy groups.

Total Formulation:

| Ingredient | Weight introduced [g] |
|---|---|
| AMMO | 60.00 |
| MTMO | 60.00 |
| Water | 6.79 |
| HCl 37% | 0.16 |
| Methanol* | 60.00 |

*Water content: 0.05%

The siloxane co-oligomer prepared according to Example 2 has a mean degree of polymerisation of 2.5 (simplified calculation; for the purposes of illustration only):

$$(n(\text{AMMO}) + n(\text{MTMO}))/[(n(\text{AMMO}) + n(\text{MTMO})) - n(\text{water})] = 0.640 \text{ mol}/[0.640 \text{ mol} - 0.384 \text{ mol}]$$
$$= 2.50$$

where n (water):(n (AMMO)+n (MTMO))×3×desired saturation in %/100×0.5.

EXAMPLE 3: SYNTHETIC FIXING MORTAR SYSTEM BASED ON OLIGOMERIC HARDENER

Component A:

| Raw material | Content [%] |
|---|---|
| Bisphenol A/F epichlorohydrin resin | 45 |
| Trimethylolpropane triglycidyl ether | 15 |
| White Portland cement | 35 |
| Various additives, pigments and rheology aids | 5 |

Component A has a viscosity of 75,000 mPa*s (Brookfield Sp. 7 at 23° C.)

Component B:

| Raw material | Content [%] |
|---|---|
| Mannich base formulation | 61 |
| 3-Aminopropylsiloxane olidomer from Example 1 | 26 |
| White Portland cement | 7 |
| Various additives, pigments and rheology aids | 6 |

Component B has a viscosity of 55,000 mPa*s (Brookfield Sp. 7 at 23° C.)

The components are subjected to an adhesion failure test, using a commercially available two-chamber cartridge with a static mixer, analogously to the conditions described in the guideline of the "European Organisation for Technical Approvals" (EOTA) (2001): ETAG No. 001 November 2006 edition, Guideline for European Technical Approval of Metal Anchors for Use in Concrete, Part 5: Bonded Anchors, February 2008, under 5.1.2.1 (b). The mean value of the adhesion failure load from five tests for M12 bolts at an anchoring depth of 72 mm is 90.5 kN.

The invention claimed is:

1. A method for fixing anchoring elements in a hole or crevice, in which a synthetic fixing mortar system and an anchoring means are introduced successively or substantially simultaneously into the hole or crevice in a substrate, wherein said synthetic fixing mortar system is hardenable by addition polymerisation and includes a hardener composition and a hardenable epoxy- and/or isocyanate-based reactive synthetic resin, wherein said hardener composition includes oligomeric siloxanes having on average per molecule at least one organic radical that carries one or more secondary and/or primary amino and/or thiol groups and having on average per molecule one or more hydrolysable groups, and optionally one or more additives.

2. The method according to claim 1, wherein the proportion of hardener composition is from 10 to 80% by weight based on the total mass of the reactants and additives of the synthetic fixing mortar system.

3. The method according to claim 1, wherein a hardenable epoxy-based reactive synthetic resin is included.

4. The method according to claim 1, wherein the hardenable epoxy-based reactive synthetic resin is selected from those based on glycidyl compounds, which optionally includes further glycidyl ether(s) as reactive diluent.

5. The method according to claim 4, wherein the glycidyl compounds have an average glycidyl group functionality of 1.5 or greater.

6. The method according to claim 4, including as reactive diluent poly(including di)-glycidyl ethers at least one polyvalent alcohol or phenol.

7. The method according to claim 1, wherein a hardenable isocyanate-based reactive synthetic resin is included.

8. The method according to claim 1, wherein the hardenable isocyanate-based reactive synthetic resin is selected from mono-, di- or poly-isocyanates and isocyanate prepolymers.

9. The method according to claim 1, wherein, in addition to the hardener composition, further hardeners are included therein, selected from
   di- or poly-amines; and
   di- or poly-thiols.

10. The method according to claim 9, wherein
    the di- or poly-amines are selected from the group consisting of aliphatic, heteroaliphatic, cycloaliphatic, araliphatic and aromatic di- or poly-amines, amidoamines, amine adducts, polyether diamines, Mannich bases, and polyphenyl/polymethylene-polyamines, alone or in admixture with one or more further di- or poly-amines, and/or polyamides, and
    the di- or poly-thiols are selected from the group consisting of ethoxylated and/or propoxylated alcohols of mono-, di-, tri-, tetra-, penta-ols and/or other polyols with thiol end groups and thiols that include ester groups.

11. The method according to claim 1, wherein the synthetic fixing mortar system is a multi-component system.

12. The method according to claim 1, wherein the oligomeric siloxanes are siloxane oligomers which are functionalised with amino and/or thiol groups and which have per molecule of oligomer at least two or more amino and/or thiol groups and at least one hydrolysable group bonded to silicon and have Si—O-crosslinked structural elements which form at least one structure selected from chain-like, cyclic and crosslinked structures.

13. The method according to claim 12, comprising at least two of the hydrolysable groups.

14. The method according to claim 1, wherein the oligomeric siloxanes include at least one structure of the general formula (I), $$(R^1O)[(R^1O)_{\{2-(a+e)\}}(R^2)_a Si(A)_e O]_b—[Si(Y)_2 O]_c—[Si(B)_e(R^4)_d(OR^3)_{\{2-(d+e)\}}O]_f R^3 \quad (I)$$

wherein compounds of the general formula (I) are derived from alkoxysilanes and

A and B each independently of the other are alkyl that includes at least one (primary or secondary) amino and/or thiol group;

Y denotes $OR^5$ and/or $R^5$ or, in crosslinked structures, independently of any other denotes $OR^5$, $R^5$ or, in case that two molecules of the formula (I) are linked to each other at the position of Y via one common oxygen atom, is $O_{0.5}$;

the radicals $R^1$, $R^2$, $R^3$, $R^4$ and $R^5$, each on its own and independently of one another, denote an unsubstituted or substituted—optionally hetero-atom-containing—linear, branched or cyclic alkyl radical having from 1 to 20 carbon atoms;

and a, b, c, d, e and f, based on a structural unit, independently of one another denote whole numbers, wherein a independently of any other is 0 or 1 or 2;

b is 1 or more;

c is 0 or more;

d independently of any other is 0 or 1 or 2;

e independently of any other is 1 or 2; and f is 0 or more;

with the proviso that b+c+f is 2 or more.

15. The hardener composition method according to claim 14, wherein Y is $OR^5$.

16. The method according to claim 14, wherein the oligomeric siloxanes include structural elements of the formula (I), wherein A and B are 3-aminopropyl, 3-aminopropyl-methyl, N-(2-aminoethyl)-3-aminopropyl, N-(2-aminoethyl)-3-aminopropyl-methyl, N-cyclohexyl-3-aminopropyl, N-cyclohexylaminomethyl, N-phenylaminomethyl, N-cyclohexylaminomethyl-methyl, 3-[2-(2-aminoethylamino)ethylamino]propyl and/or 3-mercaptopropyl.

* * * * *